United States Patent [19]

Kottenhahn et al.

[11] Patent Number: 5,616,727

[45] Date of Patent: Apr. 1, 1997

[54] PROCESS FOR PURIFYING 1-[N²-((S)-ETHOXYCARBONYL)-3-PHENYLPROPYL)-N⁶-TRIFLUOROACETYL]-L-LYSYL-L-PROLINE (LISINOPRIL (TFA) ETHYL ESTER

[75] Inventors: Matthias Kottenhahn; Karlheinz Drauz, both of Freigericht, Germany

[73] Assignee: Degussa Aktiengesellschaft, Germany

[21] Appl. No.: 616,885

[22] Filed: Mar. 18, 1996

[51] Int. Cl.⁶ .................................................. C07D 207/20
[52] U.S. Cl. .......................... 548/533; 548/534; 548/535
[58] Field of Search .................................... 548/533, 534, 548/535

[56] References Cited

FOREIGN PATENT DOCUMENTS

645398A1   3/1995   European Pat. Off. .

*Primary Examiner*—Johann Richter
*Assistant Examiner*—Jane C. Oswecki
*Attorney, Agent, or Firm*—Cushman Darby & Cushman Intellectual Property Group of Pillsbury Madison & Sutro

[57]                ABSTRACT

A process for purifying 1-[N²-((S)-ethoxycarbonyl)-3-phenylpropyl)-N⁶-trifluoroacetyl]-1-lysyl-1-proline by extraction and crystallization. The process includes a two step extraction in a two phase aqueous/organic solvent system and crystallization from organic solvent.

20 Claims, No Drawings

PROCESS FOR PURIFYING 1-[$N^2$-((S)-ETHOXYCARBONYL)-3-PHENYLPROPYL)-$N^6$-TRIFLUOROACETYL]-L-LYSYL-L-PROLINE (LISINOPRIL (TFA) ETHYL ESTER

BACKGROUND OF THE INVENTION

1. Field of the Invention

The invention is relative to a process for purifying 1-[$N^2$-((S)-ethoxycarbonyl)-3-phenylpropyl)-$N^6$-trifluoroacetyl]-1-lysyl-1-proline (compound I) by extraction and crystallization.

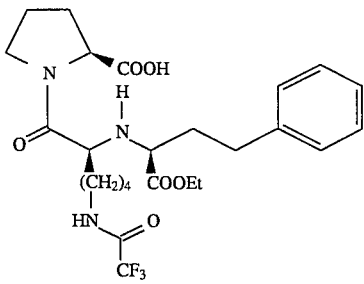

2. Background Information

N-substituted amino acids of this type are valuable intermediates for the production of inhibitors of the angiotensin converting enzyme (ACE), which act as blood-pressure regulators. Compound I is the direct intermediate product for 1-[$N^2$-((S)-carboxyl)-3-phenylpropyl)]-L-lysyl-L-proline (lisinopril) compound II, which displays excellent therapeutic results in the combatting of high blood pressure (Zerstril®, Coric®, prinivil®).

Compound I is obtained according to the state of the art by the reductive amination of 2-oxo-4-phenyl-ethyl butyrate with the dipeptide Lys(Tfa)Pro.

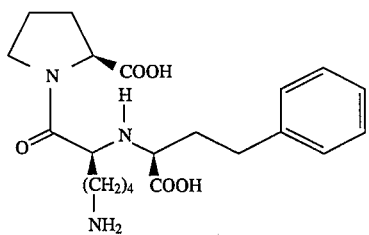

Such a process is described in J. Org. Chem. 1988, 53, 836–844. According to this passage, compound I is obtained in a yield of 42% by basic extraction of the raw reaction solution, a subsequent extraction of the product into an organic solvent at pH 4.6 and succeeding crystallization from methyl-tert.butyl ether, cyclohexane.

DE-OS 41 23 248 is relative to the synthesis of compound I, which is obtained according to example 3 in a yield of 60%. The workup of the raw reaction solution obtained according to this process includes, in addition to a basic and an acidic extraction step, a crystallization from methyl-tert.butyl ether. Other processes for producing compound I are also known which are not based on reductive amination but are less advantageous (EP 0,336,368 A2).

However, the basic extraction—an extraction of the aqueous product phase is necessary in order to remove impurities out of the amination reaction —is always associated with product losses by amide- and/or ester splitting of compound I to compound II and of compound I to compounds III and IV.

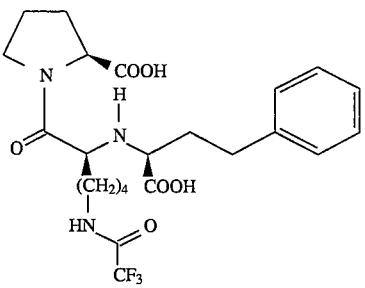

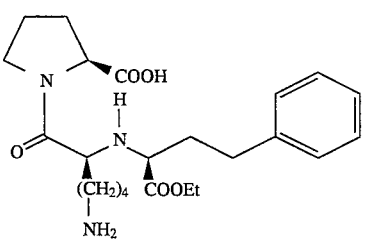

In order to minimize these product losses, the work must be performed at pH's precisely adjusted, at low temperatures, and with the shortest possible contact times. This is complicated and produces problems, especially on an industrial scale.

The crystallization from methyl-tert.butyl ether is therefore associated with high yield losses since the crystallization must be carried out in high dilution in order to be able to directly obtain the diastereomerically pure compound (I), which reduces the yield. If (I) is allowed to crystallize from solutions with high concentration, an additional recrystallization is necessary. The addition of cyclohexane (J. Org. Chem., 1988, 53, 836–844) during the crystallization is also described for raising the yield. However, there is the danger here of a separation of the product as oil, which makes it much more difficult to isolate the product, not only on an industrial scale.

SUMMARY OF THE INVENTION

It is an object of the invention to provide an improved process for purifying (I).

This object is achieved by extracting the raw product of (I) which is obtained after reductive amination by evaporating the reaction solution. The extraction is carried out (repeatedly, if necessary) with a two-phase system of water-solvent whose aqueous phase is adjusted to a pH between 0 and 3.5, preferably between 0.5 and 2. After the separation of the organic phase the remaining aqueous solution is adjusted with an alkalinizing compound, NaOH or KOH being preferred, to a pH between 3.5 and 6.3, and preferably between 3.9 and 4.8. The aqueous solution is subsequently extracted with an organic solvent or solvent mixture nonmiscible with water, multiply if necessary and the oily product is isolated from the organic phase (I) by evaporation. After being dissolved in a mixture of methyl-tert.butyl ether and methylcyclohexane, the product (I) is allowed to crystallize out by cooling to temperatures of –40° C. to +50° C., especially –10° C. to 30° C.

The crystalline product is then separated by known methods.

The acidic extraction of the aqueous product solution surprisingly results in product losses which are hardly noticeable and simultaneous high purification of the aqueous product phase even though the trifluoroacetylamide function can be split off even in the acidic medium. The solution also unexpectedly proved to be stable in an acidic environment for rather long time periods (~48 h), which constitutes a significant technical simplification. An advantageous pH range of the acidic extraction is located between 0 and 3.5 and a range between 0.5 and 2 is especially advantageous. The extraction can be carried out at temperatures between 0° C. and 60° C., preferably between 10° C. and 40° C., and more preferably at room temperature. Solvents which are non-miscible with water, including but not limited to toluene, methyl-tert.butylether, ethyl acetate, isopropyl acetate, methylene chloride, trichloroethane, chloroform and mixtures thereof, can be used as extraction solvents.

The temperature ranges and solvent/solvent mixtures described above also apply to the 2nd extraction step.

The recrystallization of product (I) takes place in accordance with the process of the invention from a mixture of methyl-tert.butyl ether and methylcyclohexane at lowered temperatures. A pro-crystallization at the temperatures indicated below from methyl-tert.butyl ether with subsequent addition of methylcyclohexane for completing the crystallization is especially advantageous. The addition of methylcyclohexane results in distinctly purer products with a distinctly reduced tendency to separate the product as oil than was possible according to the start of the art. The volume ratio of methyl-tert.butyl ether to methylcyclohexane varies thereby from 1:1 to 20:1 and a ratio of 2:1 to 10:1 is especially advantageous. The crystallization takes place at temperatures between −0° C. and 50° C., especially advantageously between −10° C. and 30° C.

The concentration range, expressed as the ratio of g product (I) to ml solvent individually (methyl-tert.butyl ether) or conjointly (with methylcyclohexane), is 1:0.5 to 1:30, preferably 1:1 to 1:10, as a function, of course, of the solubilities given by the temperature.

DETAILED DESCRIPTION OF THE INVENTION

The process of the invention is explained in detail in the following examples.

Example 1

1-[$N^2$-((S)-ethoxycarbonyl)-3-phenylpropyl)-$N^6$-trifluoroacetyl]-L-lysyl-L-proline (compound I)

A reductive amination according to Patent Application P 41 23 248.8 is carried out in analogy with example 3, page 10, therein.

Workup

The reaction solution of a 150 mmole batch was largely evaporated in a vacuum at a 45° C. bath temperature. The residue was taken up in 750 ml water and briefly stripped in a vacuum. After the addition of 150 ml 1,1,1-trichloroethane the pH was adjusted to 1 with conc. HCl. The mixture was agitated 10 min and the phases subsequently separated. The pH of the aqueous phase was adjusted to 4.6, and it was extracted 2× with 300 ml 1,1,1-trichloroethane.

The organic phase was evaporated in a vacuum and taken up in 250 ml methyl-tert.butyl ether. A thick crystalline pulp was produced by cooling off to 5° C. and seeding, which pulp was compounded after 5 hours under vigorous agitation with 65 ml methylcyclohexane. After a further 2 h at 5° C. the matter was removed by suction and dried in a vacuum.

Yield: 54 g (67.5% of theoretical), SSS diastereomer content: >99%, $[\alpha]_D^{20}$: −25.6° [(c=1 in MeOH/HCl (1:1)].

Example 2

1-[$N^2$-((S)-ethoxycarbonyl)-3-phenylpropyl)-$N^6$-trifluoroacetyl]-L-lysyl-L-proline (compound I)

A reductive amination according to Patent Application P 41 23 248.8 is carried out in analogy with example 3, page 10, therein.

Workup

The reaction solution of a 150 mmole batch was largely evaporated in a vacuum at a 45° C. bath temperature. The residue was taken up in 750 ml water and briefly stripped in a vacuum. After the addition of 120 ml toluene and 30 ml ethyl acetate the pH was adjusted to 1 with conc. HCl. The mixture was agitated 10 min and the phases subsequently separated. The pH of the aqueous phase was adjusted to 4.6 and it was extracted 1× with 400 ml ethyl acetate.

The organic phase was evaporated in a vacuum and taken up in 250 ml methyl-tert.butyl ether. A thick crystalline pulp was produced by cooling off to 5° C. and seeding, which pulp was compounded after 5 hours under vigorous agitation with 65 ml methylcyclohexane. After a further 2 h at 5° C. the matter was removed by suction and dried in a vacuum.

Yield: 54 g (68% of theoretical), SSS diastereomer content: >99 %, $[\alpha]_D^{20}$: −25.5° [(c=1 in MeOH/HCl (1:1)].

References cited herein are hereby incorporated by reference.

What is claimed is:

1. A process for purifying a 1-[$N^2$-((S)-ethoxycarbonyl)-3-phenylpropyl)-$N^6$-trifluoroacetyl]-1-lysyl-1-proline (I) raw product obtained by reductive amination, by means of two extraction steps with organic solvent and crystallization from methyl-tert. butyl ether, comprising i) treating the raw product in a first extraction step with a two-phase system of water-solvent whose aqueous phase is adjusted to a pH between 0 and 3.5 and retaining a resulting aqueous phase therefrom;

ii) adjusting the resulting aqueous phase with an alkalinizing compound to a pH between 3.5 and 6.3 and treating said aqueous phase with an organic solvent or solvent mixture non-miscible with water in a second extraction step and retaining a resulting solvent phase therefrom; and iii) crystallizing 1-[$N^2$-((S)-ethoxycarbonyl)-3-phenylpropyl)-$N^6$-trifluoroacetyl]-1-lysyl-1-proline (I) from said resulting solvent phase with addition of methylcycloxexane.

2. The method according to claim 1, wherein the first extraction step is carried out in a pH range of 0.5 to 2.

3. The method according to claim 1 wherein a mixture of toluene and ethyl acetate is used as organic solvent in the first extraction step.

4. The method according to claim 2 wherein a mixture of toluene and ethyl acetate is used as organic solvent in the first extraction step.

5. The method according claim 1 wherein (I) is first allowed to pre-crystallize out of methyl-tert.butyl ether and the crystallization is subsequently completed by adding methylcyclohexane.

6. The method according claim 2 wherein (I) is first allowed to pre-crystallize out of methyl-tert.butyl ether and that the crystallization is subsequently completed by adding methylcyclohexane.

7. The method according to claim 3 wherein (I) is first allowed to pre-crystallize out of methyl-tert.butyl ether and that the crystallization is subsequently completed by adding methylcyclohexane.

8. The method according claim 4 wherein (I) is first allowed to pre-crystallize out of methyl-tert.butyl ether and that the crystallization is subsequently completed by adding methylcyclohexane.

9. The method according to claim 1 wherein the volume ratio between methyl-tert. butyl ether and methylcyclohexane is between 1:1 and 20:1.

10. The method according to claim 3 wherein the volume ratio between methyl-tert. butyl ether and methylcyclohexane is between 1:1 and 20:1.

11. The method according to claim 6 wherein the volume ratio between methyl-tert. butyl ether and methylcyclohexane is between 1:1 and 20:1.

12. The method according to claim 8 wherein the volume ratio between methyl-tert. butyl ether and methylcyclohexane is between 1:1 and 20:1.

13. The method according to claim 1, wherein the volume ratio between methyl-tert. butyl ether and methylcyclohexane is between 2:1 and 10:1.

14. The method according to claim 6, wherein the volume ratio between methyl-tert. butyl ether and methylcyclohexane is between 2:1 and 10:1.

15. The method according to claim 8, wherein the volume ratio between methyl-tert. butyl ether and methylcyclohexane is between 2:1 and 10:1.

16. The method according to claim 1, wherein crystallization is allowed to take place in a temperature range between −40° C. and 50° C.

17. The method according to claim 6, wherein crystallization is allowed to take place in a temperature range between −40° C. and 50° C.

18. The method according to claim 8, wherein crystallization is allowed to take place in a temperature range between −40° C. and 50° C.

19. The method according to claim 16, wherein crystallization is allowed to take place in a temperature range between −10° C. and 30° C.

20. The method according to claim 18, wherein crystallization is allowed to take place in a temperature range between −10° C. and 30° C.

\* \* \* \* \*

UNITED STATES PATENT AND TRADEMARK OFFICE
CERTIFICATE OF CORRECTION

PATENT NO. : 5,616,727
DATED : April 1, 1997
INVENTOR(S) : Kottenhahn et al

It is certified that error appears in the above-indentified patent and that said Letters Patent is hereby corrected as shown below:

On the title page: after Item [22], please insert Item [30] Foreign Application Priority Data:

Sep. 17, 1993 [DE] Germany ...............4331540.2
Aug. 19, 1994 [WO] WIPO .................PCT/EP94/02760

Signed and Sealed this

Fourteenth Day of October, 1997

Attest:

BRUCE LEHMAN

Attesting Officer

Commissioner of Patents and Trademarks